United States Patent
Laroche et al.

(10) Patent No.: US 10,675,607 B2
(45) Date of Patent: Jun. 9, 2020

(54) ZEOLITIC ADSORBENTS WITH LARGE EXTERNAL SURFACE AREA, PROCESS FOR PREPARING THEM AND USES THEREOF

(71) Applicants: Arkema France, Colombes (FR); IFP Energies Nouvelles, Rueil-Malmaison (FR)

(72) Inventors: Catherine Laroche, Vernaison (FR); Philibert Leflaive, Mions (FR); Ludivine Bouvier, Orthez (FR); Serge Nicolas, Lons (FR); Cecile Lutz, Gan (FR); Marie-Laurence Labede, Lescar (FR)

(73) Assignees: Arkema France, Colombes (FR); IFP Energies Nouvelles, Rueil-Malmaison (FR)

( * ) Notice: Subject to any disclaimer, the term of this patent is extended or adjusted under 35 U.S.C. 154(b) by 317 days.

(21) Appl. No.: 15/880,201

(22) Filed: Jan. 25, 2018

(65) Prior Publication Data

US 2018/0161754 A1   Jun. 14, 2018

Related U.S. Application Data

(62) Division of application No. 14/917,457, filed as application No. PCT/EP2014/068993 on Sep. 5, 2014, now Pat. No. 9,914,109.

(30) Foreign Application Priority Data

Sep. 9, 2013 (FR) ...................... 13 58662
Sep. 10, 2013 (FR) ...................... 13 58715

(51) Int. Cl.

| | |
|---|---|
| B01D 53/02 | (2006.01) |
| B01D 53/08 | (2006.01) |
| B01J 20/12 | (2006.01) |
| B01J 20/18 | (2006.01) |
| B01J 20/28 | (2006.01) |
| B01J 20/30 | (2006.01) |
| C07C 15/02 | (2006.01) |
| C07C 15/08 | (2006.01) |
| C07C 201/16 | (2006.01) |
| C07C 205/06 | (2006.01) |
| C07C 209/86 | (2006.01) |
| C07C 211/50 | (2006.01) |
| C07C 29/76 | (2006.01) |
| C07C 37/82 | (2006.01) |
| C07C 39/07 | (2006.01) |
| C07C 7/13 | (2006.01) |

(52) U.S. Cl.
CPC .............. *B01J 20/18* (2013.01); *B01D 53/02* (2013.01); *B01D 53/08* (2013.01); *B01J 20/12* (2013.01); *B01J 20/186* (2013.01); *B01J 20/28004* (2013.01); *B01J 20/28059* (2013.01); *B01J 20/28061* (2013.01); *B01J 20/28071* (2013.01); *B01J 20/3028* (2013.01); *B01J 20/3071* (2013.01); *B01J 20/3085* (2013.01); *C07C 7/13* (2013.01); *C07C 29/76* (2013.01); *C07C 37/82* (2013.01); *C07C 201/16* (2013.01); *C07C 209/86* (2013.01); *B01D 2253/108* (2013.01); *B01D 2257/556* (2013.01)

(58) Field of Classification Search
None
See application file for complete search history.

(56) References Cited

U.S. PATENT DOCUMENTS

| | | | |
|---|---|---|---|
| 2,985,589 | A | 5/1961 | Broughton et al. |
| 3,558,730 | A | 1/1971 | Neuzil |
| 3,558,732 | A | 1/1971 | Neuzil |
| 3,626,020 | A | 12/1971 | Neuzil |
| 3,663,638 | A | 5/1972 | Neuzil |
| 3,878,127 | A | 4/1975 | Rosback |
| 3,960,774 | A | 6/1976 | Rosback |
| 4,402,832 | A | 9/1983 | Gerhold |
| 4,498,991 | A | 2/1985 | Oroskar |
| 5,284,992 | A | 2/1994 | Hotier et al. |
| 5,629,467 | A | 5/1997 | Hotier et al. |
| 7,785,563 | B2 | 8/2010 | Ryoo et al. |
| 2009/0326308 | A1 | 12/2009 | Kulprathipanja et al. |
| 2012/0247334 | A1 | 10/2012 | Hurst et al. |

FOREIGN PATENT DOCUMENTS

| | | |
|---|---|---|
| CN | 1267185 C | 8/2006 |
| FR | 2789914 A1 | 8/2000 |
| FR | 2903978 A1 | 1/2008 |

(Continued)

OTHER PUBLICATIONS

Ruthven, D. et al., "Principles of adsorption and adsorption processes," 1984, pp. 243, 326 & 407, 248-250, John Wiley & Sons.

(Continued)

*Primary Examiner* — Colin W. Slifka
(74) *Attorney, Agent, or Firm* — RatnerPrestia

(57) ABSTRACT

The present invention relates to zeolitic adsorbents based on agglomerated crystals of FAU zeolite containing barium and/or potassium, with large external surface area, combining optimum properties in terms of selectivity and mechanical strength. These adsorbents find applications in the separation of cuts of C8-aromatic isomers and notably of xylenes, in the separation of isomers of substituted toluene such as nitrotoluene, diethyltoluene, toluenediamine, in the separation of cresols, and in the separation of polyhydric alcohols such as sugars.

19 Claims, No Drawings

(56) References Cited

FOREIGN PATENT DOCUMENTS

WO    20070043731  A1    4/2007
WO    20130106816  A1    7/2013

OTHER PUBLICATIONS

Inayat, A., et al., "Assemblies of mesoporous FAU-type zeolite nanosheets," Angewandte Chemie International Edition, vol. 51, No. 8, Feb. 20, 2012, pp. 1962-1965.

Verboekend, D., et al., "Hierarchical Y and USY zeolites designed by post-synthetic strategies," Advanced Functional Materials, vol. 22, No. 5, Mar. 7, 2012, pp. 916-928.

International Search Report and Written Opinion of the International Searching Authority for International Application No. PCT/EP2014/068993 dated Oct. 8, 2014, 10 pages.

Linares, et al., "K and $Ca^{2+}$ modified Na-X zeolites as possible bile acids sequestrant," Journal of Materials Science: Materials in Medicine, 2007, vol. 19, No. 5, pp. 2023-2028.

Entire patent prosecution history of U.S. Appl. No. 14/917,457, filed Mar. 8, 2016, entitled, "Zeolitic Adsorbents With Large External Surface Area, Process for Preparing Them and Uses Thereof," now U.S. Pat. No. 9,914,109, dated Mar. 13, 2018.

Non Final Office Action for U.S. Appl. No. 14/917,457, dated May 9, 2017, 11 pages.

Notice of Allowance for U.S. Appl. No. 14/917,457, dated Oct. 27, 2017, 9 pages.

ZEOLITIC ADSORBENTS WITH LARGE EXTERNAL SURFACE AREA, PROCESS FOR PREPARING THEM AND USES THEREOF

CROSS-REFERENCE TO RELATED APPLICATIONS

This application is a divisional of U.S. application Ser. No. 14/917,457, filed 8 Mar. 2016, now U.S. Pat. No. 9,914,109, which is the national phase of International Application No. PCT/EP2014/068993, filed 5 Sep. 2014, which claims priority from French Applications Nos. FR1358662 (filed 9 Sep. 2013) and FR1358715 (filed 10 Sep. 2013). The disclosures of each of these applications are incorporated herein by reference in their entirety for all purposes.

FIELD OF THE INVENTION

The invention relates to adsorbents in the form of agglomerates comprising zeolite of the faujasite type, said adsorbents having a large external surface area characterized by nitrogen adsorption typically greater than 20 $m^2 \cdot g^{-1}$, and preferably between 40 $m^2 \cdot g^{-1}$ and 200 $m^2 \cdot g^{-1}$.

The present invention also relates to a process for preparing said zeolitic adsorbents having a large external surface area, as well as uses thereof for separating gaseous or liquid mixtures of isomers, more particularly of xylenes and notably for producing very pure para-xylene starting from a feed of aromatic hydrocarbons containing isomers with 8 carbon atoms.

BACKGROUND OF THE RELATED ART

The use of zeolitic adsorbents consisting of faujasite (FAU) zeolites of type X or Y comprising, besides sodium cations, barium, potassium or strontium ions, alone or mixed, for selectively adsorbing para-xylene in a mixture of aromatic hydrocarbons, is well known from the prior art.

Patents U.S. Pat. Nos. 3,558,730, 3,558,732, 3,626,020 and 3,663,638 show that zeolitic adsorbents comprising aluminosilicates based on sodium and barium (U.S. Pat. No. 3,960,774) or based on sodium, barium and potassium, are effective for separating para-xylene present in C8 aromatic cuts (cuts comprising aromatic hydrocarbons with 8 carbon atoms).

The adsorbents described in patent U.S. Pat. No. 3,878,127 are used as adsorption agents in liquid-phase processes, preferably of the simulated countercurrent type, similar to those described in patent U.S. Pat. No. 2,985,589, and which are applied to the C8 aromatic cuts, among others.

In the patents listed above, the zeolitic adsorbents are in the form of crystals in the powder state or in the form of agglomerates constituted predominantly of zeolite powder and up to 20 wt % of inert binder.

The FAU zeolites are usually synthesized by nucleation and crystallization of aluminosilicate gels. This synthesis leads to crystals (generally in the form of powder) whose use on an industrial scale is particularly difficult (large head losses during the operations). Therefore the agglomerated forms of these crystals are preferred, in the form of grains, spun yarn and other agglomerates, said forms being obtainable by extrusion, pelletization, spraying and other agglomeration techniques known by a person skilled in the art. These agglomerates do not have the inherent drawbacks of the pulverulent materials.

Moreover, the zeolite crystals are most often prepared from aqueous soda solutions (for example aqueous solution of sodium hydroxide), and, if desired, the sodium cations may be replaced (exchanged) wholly or partly with other cations, for example barium or barium and potassium. These cationic exchanges may be carried out before and/or after agglomeration of the pulverulent zeolite with the agglomeration binder, by conventional techniques known by a person skilled in the art.

The agglomerates, whether they are in the form of platelets, beads, extrudates, and others, generally consist of crystals of zeolite(s), which constitute the active element (in the sense of adsorption), and an agglomeration binder. This agglomeration binder is intended to provide cohesion of the crystals with one another in the agglomerated structure, but must also be able to endow said agglomerates with sufficient mechanical strength so as to avoid, or at the very least minimize as far as possible, the risks of fractures, splintering or breaks that might occur in industrial uses, during which the agglomerates are subjected to many stresses, such as vibrations, large and/or frequent pressure changes, movements etc.

These agglomerates are prepared for example by forming a paste of zeolite crystals in powder form with a clay slip, in proportions of the order of 80 to 90 wt % of zeolite powder to 20 to 10 wt % of binder, then forming as beads, platelets or extrudates, and thermal treatment at high temperature for baking the clay and reactivation of the zeolite, moreover the cationic exchange(s), for example exchange with barium, may be carried out before and/or after agglomeration of the pulverulent zeolite with the binder.

Zeolite bodies are obtained whose grain size is of some millimetres, or even of the order of a millimetre, and which, if selection of the agglomeration binder and granulation are done according to standard procedures, have a satisfactory set of properties, in particular of porosity, mechanical strength, and abrasion resistance. However, the adsorption properties of these agglomerates are of course reduced relative to the starting active powder owing to the presence of the agglomeration binder, which is inert with respect to adsorption.

Various means have already been proposed for overcoming this drawback of the agglomeration binder being inert as regards adsorption performance, including transformation of all or at least a proportion of the agglomeration binder into zeolite that is active from the standpoint of adsorption. This operation is now well known by a person skilled in the art, for example by the name "zeolitization". So that this operation can be performed easily, zeolitizable binders are used, most often belonging to the kaolinite family, and preferably calcined beforehand at temperatures generally between 500° C. and 700° C.

Patent application FR2789914 describes a process for manufacturing agglomerates of zeolite X, of Si/Al atomic ratio between 1.15 and 1.5, exchanged with barium and optionally with potassium, agglomerating crystals of zeolite X with a binder, a source of silica and carboxymethylcellulose, and then zeolitizing the binder by immersing the agglomerate in an alkaline solution. After exchange of the cations of the zeolite with barium (and optionally potassium) ions and activation, the agglomerates thus obtained have, from the standpoint of the adsorption of para-xylene contained in C8 aromatic cuts, improved properties relative to adsorbents prepared from the same amount of zeolite X and binder, but whose binder has not been zeolitized.

In addition to high adsorption capacity and good properties of selectivity for the species to be separated from the reaction mixture, the adsorbent must have good properties of mass transfer in order to guarantee a sufficient number of theoretical plates for performing effective separation of the species in the mixture, as stated by Ruthven in the work with the title "*Principles of Adsorption and Adsorption Processes*", John Wiley & Sons, (1984), pages 326 and 407. Ruthven states (ibid., page 243) that, in the case of an agglomerated adsorbent, the total mass transfer depends on the sum of the intracrystalline diffusion resistance and the diffusion resistance between the crystals.

The intracrystalline diffusion resistance is proportional to the square of the diameters of the crystals and inversely proportional to the intracrystalline diffusivity of the molecules to be separated.

The diffusion resistance between the crystals (also called "macroporous resistance"), for its part, is proportional to the square of the diameters of the agglomerates, inversely proportional to the porosity contained in the macropores and mesopores (i.e. the pores with width larger than 2 nm) within the agglomerate, and inversely proportional to the diffusivity of the molecules to be separated in this porosity.

The size of the agglomerates is an important parameter when the adsorbent is used in an industrial application, as it determines the head loss within the industrial unit and the uniformity of filling. The agglomerates must therefore have a narrow granulometric distribution, centred on number-average diameters typically between 0.40 mm and 0.65 mm in order to avoid excessive head losses. The porosity contained in the macropores and mesopores does not contribute to the adsorption capacity. Consequently, a person skilled in the art will not try to increase it with the aim of reducing the macroporous diffusion resistance, knowing that this would be to the detriment of the volumetric adsorption capacity.

To estimate the improvement in transfer kinetics, it is possible to use the plate theory described by Ruthven in "*Principles of Adsorption and Adsorption Processes*", ibid., pages 248-250. This approach is based on the representation of a column by a finite number of ideally stirred hypothetical reactors (theoretical stages). The height equivalent to a theoretical plate is a direct measure of the axial dispersion and of the resistance to mass transfer of the system.

For a given zeolitic structure, a given size of agglomerate and a given operating temperature, the diffusivities are fixed, and one way of improving the mass transfer consists of reducing the diameter of the crystals. A gain in total mass transfer will thus be obtained by reducing the size of the crystals.

A person skilled in the art will therefore try to reduce the diameter of the zeolite crystals as much as possible in order to improve mass transfer.

Patent CN1267185C thus claims adsorbents containing 90% to 95% of zeolite BaX or BaKX for separating para-xylene, in which the crystals of zeolite X have a size between 0.1 µm and 0.4 µm, in order to improve the mass transfer performance. Moreover, patent US20090326308 describes a method for separating xylene isomers, the performance of which was improved by using adsorbents based on crystals of zeolite X smaller than 0.5 µm.

The applicant has observed, however, that the synthesis, filtration, manipulation and agglomeration of zeolite crystals smaller than 0.5 µm employ methods that are arduous, rather uneconomical and therefore difficult to apply industrially.

Moreover, such agglomerates comprising crystals smaller than 0.5 µm also prove to be more fragile, and so it becomes necessary to increase the level of agglomeration binder in order to strengthen the cohesion of the crystals with one another within the agglomerate. However, increasing the level of agglomeration binder leads to densification of the agglomerates, causing an increase in the macroporous diffusion resistance. Thus, although the intracrystalline diffusion resistance is reduced owing to the decrease in size of the crystals, the increase in the macroporous diffusion resistance as a result of the densification of the agglomerate does not allow an improvement in overall transfer.

Consequently there is still a need for zeolitic adsorbent materials prepared from FAU type zeolite that is easy to handle in an industrial context, i.e. whose constituent crystalline elements (or more simply "crystals") are advantageously larger than 0.5 µm, but displays a total mass transfer that is improved relative to an adsorbent prepared from conventional zeolite crystals of the FAU type of identical size (i.e. above 0.5 µm), while still having a high adsorption capacity.

These improved adsorbents would thus be particularly suitable for gas-phase or liquid-phase separation of xylene isomers.

BRIEF SUMMARY OF THE INVENTION

As its first aim, the present invention thus proposes zeolitic adsorbents in the form of agglomerates with optimized properties for the separation of gaseous or liquid mixtures of isomers and more particularly for the gas-phase or liquid-phase separation of the xylenes, notably of para-xylene from C8 aromatic cuts. The zeolitic adsorbents of the invention notably have maximum properties of selectivity with respect to para-xylene and of mass transfer, while displaying high mechanical strength and high adsorption capacity and are particularly suitable for use in a process for liquid-phase separation of para-xylene, preferably of the simulated countercurrent type.

DETAILED DESCRIPTION OF CERTAIN EMBODIMENTS OF THE INVENTION

More precisely, the present invention relates to a zeolitic adsorbent comprising at least one FAU zeolite and comprising barium and/or potassium, characterized in that the external surface area of said zeolitic adsorbent, measured by nitrogen adsorption, is above 20 $m^2 \cdot g^{-1}$, preferably above 40 $m^2 \cdot g^{-1}$, and more preferably between 40 $m^2 \cdot g^{-1}$ and 200 $m^2 \cdot g^{-1}$, and even more preferably between 60 $m^2 \cdot g^{-1}$ and 200 $m^2 \cdot g^{-1}$ inclusive.

According to yet another embodiment of the invention, the zeolitic adsorbent has a content of barium oxide (BaO) above 10%, preferably above 15%, very preferably above 20%, even more preferably above 23%, or even above 33% by weight relative to the total weight of the adsorbent. Advantageously, the barium content is between 23% and 42%, and typically between 30% and 40%, inclusive, by weight relative to the total weight of the adsorbent.

According to another embodiment of the invention, the zeolitic adsorbent may have a content of potassium oxide $K_2O$ below 25%, preferably between 0 and 20%, even more preferably between 0% and 15% and very preferably from 0% to 10% inclusive by weight relative to the total weight of the adsorbent.

According to another embodiment of the invention, the total content of oxides of alkali-metal or alkaline-earth ions other than barium oxide BaO and potassium oxide $K_2O$ is between 0 and 5% inclusive, relative to the total weight of the adsorbent.

Preferably the zeolitic adsorbent according to the present invention is an adsorbent based on FAU zeolite(s), generally referred to as zeolite X. "Zeolite X" means a zeolite whose Si/Al atomic ratio is between 1.00 and 1.50 inclusive, preferably between 1.05 and 1.50, preferably between 1.05 and 1.40 inclusive, and even more preferably between 1.10 and 1.40 inclusive.

Among the zeolites X, two subgroups are now commonly recognized, called zeolites LSX and zeolites MSX. Zeolites LSX have an Si/Al atomic ratio equal to about 1 and zeolites MSX have an Si/Al atomic ratio between about 1.05 and about 1.15, inclusive.

According to a preferred embodiment of the present invention, zeolite X has an Si/Al atomic ratio between 1.10 and 1.50, inclusive. According to another preferred embodiment, zeolite X is a zeolite of the LSX type with Si/Al atomic ratio equal to about 1. It may also be envisaged that the adsorbent contains mixtures of two or more types of zeolites X as they have just been defined.

According to a preferred embodiment, the at least one FAU zeolite comprised in the zeolitic adsorbent of the invention has an Si/Al atomic ratio between 1.00 and 1.50 inclusive, preferably between 1.05 and 1.40 and even more preferably between 1.10 and 1.40. Preferably, the at least one FAU zeolite is a zeolite X.

According to another preferred embodiment, no zeolitic structure other than the FAU structure, and preferably no zeolitic structure other than the faujasite X structure, is detected by X-ray diffraction (known by a person skilled in the art by the acronym XRD) in the zeolitic adsorbent of the present invention.

According to yet another preferred embodiment, the fraction by weight of FAU zeolite, the FAU zeolite preferably being a zeolite X, is greater than or equal to 80% relative to the total weight of adsorbent of the present invention, the complement to 100% preferably consisting of non-zeolitic phase.

The zeolitic adsorbents according to the present invention may contain a non-zeolitic phase (NZP), i.e. a non-crystalline phase which is essentially inert with respect to adsorption. The degree of crystallinity (fraction by weight of zeolite) of the adsorbent according to the invention may be measured by X-ray diffraction analysis, known by a person skilled in the art by the acronym XRD.

According to a preferred embodiment, the zeolitic adsorbent according to the invention has a loss on ignition measured at 900° C. according to standard NF EN 196-2 less than or equal to 7.7%, preferably between 0 and 7.7%, preferably between 3.0% and 7.7%, more preferably between 3.5% and 6.5% and advantageously between 4.5% and 6%, inclusive.

The zeolitic adsorbent according to the present invention advantageously has high mechanical strength and high adsorption capacity. The mechanical strength is measured by the Shell series SMS1471-74 method adapted for agglomerates smaller than 1.6 mm and is generally greater than or equal to 2 MPa, typically greater than or equal to 2.1 MPa.

The zeolitic adsorbent of the invention preferably comprises, simultaneously, macropores, mesopores and micropores. "Macropores" means pores whose width is greater than 50 nm, preferably between 50 nm and 400 nm. "Mesopores" means pores whose width is between 2 nm and 50 nm, exclusive. "Micropores" means pores whose width is less than 2 nm.

The mesopores of the zeolitic adsorbent according to the invention are easily identifiable by observation with a transmission electron microscope (TEM), as described for example in U.S. Pat. No. 7,785,563.

According to yet another preferred embodiment, the zeolitic adsorbent of the present invention is characterized by a total volume of the macropores and mesopores, measured by mercury intrusion porosimetry, advantageously between 0.15 cm$^3\cdot$g$^{-1}$ and 0.50 cm$^3\cdot$g$^{-1}$, preferably between 0.20 cm$^3\cdot$g$^{-1}$ and 0.40 cm$^3\cdot$g$^{-1}$ and very preferably between 0.20 cm$^3\cdot$g$^{-1}$ and 0.35 cm$^3\cdot$g$^{-1}$.

The volume fraction of the macropores is preferably between 0.2 and 1 of the total volume of the macropores and mesopores, very preferably between 0.4 and 0.8, and even more preferably between 0.45 and 0.65, inclusive.

In the context of the present invention, a zeolitic adsorbent is also preferred whose micropore volume, evaluated by the t-plot method from the nitrogen ($N_2$) adsorption isotherm at a temperature of 77 K, is between 0.180 cm$^3\cdot$g$^{-1}$ and 0.290 cm$^3\cdot$g$^{-1}$. Said measurement of micropore volume is calculated after degassing under vacuum (P<6.7×10$^{-4}$ Pa), at a temperature between 300° C. and 450° C. for a time in the range from 9 hours to 16 hours, preferably at 400° C. for 10 hours.

The zeolitic adsorbent of the invention is preferably in the form of an agglomerate, i.e. it consists of crystalline elements (or crystals) of at least one FAU zeolite as defined above, said crystalline elements having a number-average diameter between 0.1 μm and 20 μm, preferably between 0.5 μm and 20 μm, more preferably between 0.5 μm and 10 μm, and even more preferably between 0.5 μm and 5 μm, inclusive.

According to yet another preferred embodiment, the zeolitic adsorbent according to the invention comprises crystalline elements of FAU zeolite of type X and said zeolitic adsorbent has an Si/Al atomic ratio between 1.00 and 2.00, preferably between 1.00 and 1.80 inclusive, more preferably between 1.15 and 1.80 inclusive, and even more preferably between 1.15 and 1.60 inclusive.

As noted above, the zeolitic adsorbent according to the invention more preferably comprises at least one non-zeolitic phase (NZP), which is used in the method of preparation as agglomeration binder permitting cohesion of the crystalline elements with one another, before optionally being zeolitized completely or partially, i.e. transformed into active zeolite for adsorption of the molecules in question, i.e. converted into zeolite of the FAU type.

This signifies that the zeolitic adsorbent according to the invention preferably further comprises at least one non-zeolitic phase (NZP), which comprises among other things an agglomeration binder used in the method of preparation for ensuring cohesion of the crystals with one another, hence the term "agglomerate" or "zeolitic agglomerate" sometimes used instead of the term "zeolitic adsorbent" of the invention, as described above.

It has in fact been found by the applicant that FAU zeolitic adsorbents prepared from crystalline elements with large external surface area have improved total mass transfer relative to zeolitic adsorbents of the FAU type prepared from conventional crystals, including when the crystalline elements are larger than the conventional crystals.

The present invention therefore provides zeolitic adsorbents with improved properties relative to the prior art while facilitating filtration, handling and agglomeration of the zeolite powders used in the manufacturing process.

The invention further relates to a process for preparing said zeolitic adsorbents as they have just been defined, said process comprising at least the steps of:
a) agglomeration of crystalline elements of at least one FAU type zeolite, having an external surface area greater than 40 m$^2\cdot$g$^{-1}$, preferably between 40 m$^2\cdot$g$^{-1}$ and 400 m$^2\cdot$g$^{-1}$, more preferably between 60 m$^2 \cdot$g$^{-1}$ and 200 m$^2 \cdot$g$^{-1}$, inclusive, with number-average diameter between 0.1 μm and 20 μm, preferably between 0.5 μm and 20 μm, more preferably between 0.5 μm and 10 μm, and even more preferably between 0.5 μm and 5 μm inclusive, with a binder comprising at least 80% of clay or of a mixture of clays, optionally zeolitizable, and with up to 5% of additives as well as with the amount of water that allows forming of the agglomerated material; drying of the agglomerates at a temperature between 50° C. and 150° C.; calcination of the dried agglomerates while flushing with oxidizing and/or inert gas, notably with gases such as oxygen, nitrogen, air, dry and/or decarbonated air, oxygen-depleted air, optionally dry and/or decarbonated, at a temperature above 150° C., typically between 180° C. and 800° C., preferably between 200° C. and 650° C., for some hours, for example from 2 hours to 6 hours;

b) optionally zeolitization of some or all of the binder by bringing the agglomerates obtained in step a) into contact with an alkaline basic solution;

c) cationic exchange(s) of the agglomerates from step a) and/or from step b) by bringing into contact with a solution of barium ions and/or of potassium ions;

d) additional optional cationic exchange of the agglomerates from step c) by bringing into contact with a solution of potassium ions;

e) washing and drying the agglomerates obtained in steps c) or d), at a temperature between 50° C. and 150° C.; and f) obtaining the zeolitic adsorbent according to the invention by activation of the agglomerates obtained in step e) while flushing with oxidizing and/or inert gas, notably with gases such as oxygen, nitrogen, air, dry and/or decarbonated air, oxygen-depleted air, optionally dry and/or decarbonated, at a temperature between 100° C. and 400° C., preferably between 200° C. and 300° C. for a time determined as a function of the desired water content and loss on ignition, typically from 1 hour to 6 hours.

According to a preferred embodiment, said at least one FAU zeolite has an Si/Al atomic ratio preferably between 1.00 and 1.50, preferably between 1.05 and 1.40 and even more preferably between 1.10 and 1.40, inclusive. As noted above, the at least one FAU zeolite is preferably a zeolite X.

As noted above, the external surface area of the crystalline elements employed in step a) of the process described above is calculated by the t-plot method from the nitrogen adsorption isotherm at a temperature of 77 K, after degassing under vacuum (P<6.7×10$^{-4}$ Pa), at a temperature between 300° C. and 450° C. for a time in the range from 9 hours to 16 hours, preferably at 400° C. for 10 hours.

The crystalline elements of the FAU zeolite having a large external surface area employed in step a) may be obtained by various methods known by a person skilled in the art and for example according to the synthesis described by Inayat et al. in *Angew. Chem. Int. Ed.*, (2012), 51, 1962-1965.

It is also possible to prepare said crystalline elements by synthesis by seeding and/or by adjustment of the synthesis operating conditions such as the SiO$_2$/Al$_2$O$_3$ ratio, the sodium content and the alkalinity of the synthesis mixture or else according to conventional processes for post-treatment of FAU zeolite crystals.

The post-treatment processes generally consist of removing atoms from the zeolitic network already formed, either by one or more acid treatments which dealuminize the solid, treatment(s) followed by one or more washing(s) with soda in order to remove the alumina residues formed, as described for example by D. Verboekend, G. Vilé and J. Pérez-Ramirez, in *Adv. Funct. Mater.*, 22, (2012), p 916-928), or else by treatments that combine the action of an acid and that of a structure-forming agent, improving the effectiveness of the acid treatment, as described for example in application WO2013/106816.

The processes for direct synthesis of these zeolites (i.e. synthesis processes other than post-treatment) generally involve one or more structure-forming agents or sacrificial templates.

The sacrificial templates that can be used may be of any type known by a person skilled in the art and notably those described in application WO2007/043731. According to a preferred embodiment, the sacrificial template is advantageously selected from the organosilanes and more preferably from [3-(trimethoxysilyl)propyl]octadecyldimethylammonium chloride, [3-(trimethoxysilyl)propyl]hexadecyldimethylammonium chloride, [3-(trimethoxysilyl)propyl]dodecyldimethylammonium chloride, [3-(trimethoxysilyl)propyl]octylammonium chloride, N-[3-(trimethoxysilyl)propyl]aniline, 3-[2-(2-aminoethylamino)ethylamino]propyltrimethoxysilane, N-[3-(trimethoxysilyl)propyl]-N'-(4-vinylbenzyl)ethylenediamine, triethoxy-3-(2-imidazolin-1-yl)propylsilane, 1-[3-(trimethoxysilyl)propyl]urea, N-[3-(trimethoxysilyl)propyl]ethylenediamine, [3-(diethylamino)propyl]trimethoxysilane, (3-glycidyloxypropyl)trimethoxysilane, 3-(trimethoxysilyl)propyl methacrylate, [2-(cyclohexenyl)ethyl]triethoxysilane, dodecyltriethoxysilane, hexadecyltrimethoxysilane, (3-aminopropyl)trimethoxysilane, (3-mercaptopropyl)trimethoxysilane, (3-chloropropyl)trimethoxysilane, as well as mixtures of two or more of these in all proportions.

Among the sacrificial templates listed above, [3-(trimethoxysilyl)propyl]octadecyldimethylammonium chloride, or TPOAC, is quite particularly preferred.

It is also possible to use sacrificial templates of higher molecular weight and for example PPDA (Polymer PolyDiallyldimethylAmmonium), PVB (PolyVinyl Butyral) and other oligomeric compounds known in this field for increasing the diameter of mesopores.

According to a preferred embodiment of the process of the present invention, step a) involves the agglomeration of crystalline elements of at least one FAU zeolite with large external surface area, as described above, prepared in the presence of a sacrificial template that is intended to be removed.

Said removal may be carried out by the methods known by a person skilled in the art, for example by calcination, and without being limiting, calcination of the crystalline elements of zeolite comprising the sacrificial template may be carried out while flushing with oxidizing and/or inert gas, notably with gases such as oxygen, nitrogen, air, dry and/or decarbonated air, oxygen-depleted air, optionally dry and/or decarbonated, at a temperature or at temperatures above 150° C., typically between 180° C. and 800° C., preferably between 200° C. and 650° C., for some hours, for example between 2 and 6 hours. The nature of the gases, the temperature increase ramps and the successive temperature plateaux, and their durations, will be adapted depending on the nature of the sacrificial template.

The additional step of removal of the optional sacrificial template may be carried out at any time during the process for preparing the agglomerated zeolitic material of the invention. Removal of said sacrificial template may thus advantageously be carried out by calcination of the crystalline elements of zeolite before the agglomeration step a), or else concomitantly with calcination of the agglomerates during step a).

If the agglomeration in step a) comprised the agglomeration of several zeolites with large external surface area obtained by different methods, this would still be within the scope of the invention.

The FAU type zeolite is generally synthesized in a soda medium (Na cation). The crystalline elements of FAU zeolite thus obtained comprise predominantly, or exclusively, sodium cations. However, the use of crystalline elements that have undergone one or more cationic exchanges, between the synthesis in the Na form, before or after optional removal of the sacrificial template if this step is carried out before the application in step a) and its application in step a), would be within the scope of the invention. In this case, step c) and optionally step d) of exchange consequently become(s) unnecessary.

The size of the crystalline elements of FAU zeolite used in step a) and of the crystalline elements of FAU zeolite in the agglomerates according to the invention is measured by observation with a scanning electron microscope (SEM). As noted above, preferably, the average diameter of the elements is between 0.1 µm and 20 µm, preferably between 0.5 µm and 20 µm, more preferably between 0.5 µm and 10 µm, and even more preferably between 0.5 µm and 5 µm inclusive. This SEM observation also makes it possible to confirm the presence of non-zeolitic phase comprising for example residual binder (not converted during the zeolitization step) or any other amorphous phase in the agglomerates.

In the present document, the designation "number-average diameter" or else "size" is notably employed for the crystalline elements of zeolite and for the zeolitic adsorbents. The method of measuring these quantities is explained later on in the description.

Agglomeration and forming (step a) may be carried out by all the techniques known by a person skilled in the art, such as extrusion, compacting, agglomeration on a granulating plate, granulating drum, spraying etc.

The proportions of agglomeration binder (see definition later) and of zeolite employed are typically those of the prior art, i.e. from 5 to 20 parts by weight of binder to 95 to 80 parts by weight of zeolite.

The agglomerates resulting from step a), whether they are in the form of beads, of extrudates or other forms, generally have a number-average diameter, or their length (largest dimension when they are not spherical), between 0.2 mm and 2 mm, and in particular between 0.2 mm and 0.8 mm and preferably between 0.4 mm and 0.65 mm, inclusive.

At the end of step a) the finest agglomerates may be removed by cycloning and/or sieving and/or the agglomerates that are too large by sieving or crushing, in the case of extrudates, for example.

The binder comprised in the zeolitic agglomerated material of the present invention comprises, and preferably consists of, a clay or a mixture of clays. These clays are preferably selected from the kaolins, kaolinites, nacrites, dickites, halloysites, attapulgites, sepiolites, montmorillonites, bentonites, illites and metakaolins, as well as mixtures of two or more of them in all proportions.

In the case of the optional zeolitization step b), the agglomeration binder employed in step a) contains at least 80%, preferably at least 90%, more preferably at least 95%, more particularly at least 96%, by weight, of at least one zeolitizable clay and may also contain other mineral binders such as bentonite, attapulgite, and others. "Zeolitizable clay" means a clay or a mixture of clays that can be converted into zeolitic material, most often by the action of an alkaline basic solution. The zeolitizable clay generally belongs to the family of the kaolins, kaolinites, nacrites, dickites, halloysite and/or metakaolins. Kaolin is preferred and is used most commonly.

The additives optionally employed in step a) may include a source of silica of any type known by a person skilled in the art, specializing in the synthesis of zeolites, for example colloidal silica, diatoms, perlite, fly ash, sand, or any other form of solid silica.

In step a), besides the crystalline elements of FAU zeolite and the binder, other additives may also be added, for example additives intended to facilitate agglomeration or to improve the hardening of the agglomerates formed, such as lignin, starch, carboxymethylcellulose, and other additives known by a person skilled in the art.

For the calcination included in step a), the nature of the gases, the temperature increase ramps and the successive temperature plateaux, as well as their respective durations, will be adapted depending on the nature of the sacrificial template to be removed and depending on the nature of the binder employed in the agglomeration step a).

Especially if the agglomeration binder contains one or more zeolitizable clays, calcination makes it possible to transform the zeolitizable clay, typically kaolin, into metakaolin, which can then be converted into zeolite in the zeolitization step (step b)). The principle of this is presented in "Zeolite Molecular Sieves" of D. W. Breck, John Wiley and Sons, New York, (1973), p. 314-315.

The zeolitization of the agglomeration binder is carried out by any method that is now familiar to a person skilled in the art and may for example be carried out by immersing the product resulting from step a) in an alkaline basic solution, generally aqueous, for example an aqueous solution of sodium hydroxide and/or of potassium hydroxide.

As a general rule, the concentration of the alkaline solution for zeolitization is preferably between 0.5 M and 5 M. Zeolitization is preferably carried out hot, at a temperature above room temperature, and typically at temperatures of the order of 80° C. to 100° C., for example between room temperature (or about 20° C.) and the boiling point of the alkaline solution for zeolitization. The duration of the zeolitization process is generally between some tens of minutes and some hours, preferably between about 1 hour and 8 hours.

The steps of cationic exchange(s) c) and d) are carried out by conventional methods known by a person skilled in the art, and most often by bringing the agglomerates resulting from step a) into contact with a barium salt and/or potassium salt, such as barium chloride ($BaCl_2$) and/or potassium chloride (KCl), in aqueous solution at a temperature between room temperature and 100° C., and preferably between 80° C. and 100° C. in order to obtain high contents of barium, expressed as barium oxide, rapidly, i.e. preferably above 10%, preferably above 15%, very preferably above 20%, even more preferably above 23%, or even above 33 wt % relative to the total weight of the adsorbent.

Advantageously, the content of barium, expressed as barium oxide, is between 23% and 42%, and typically between 30% and 40% inclusive, by weight relative to the total weight of the adsorbent. It is preferable to work with a large excess of barium ions relative to the cations of the zeolite that we wish to exchange, typically an excess of the order of 10 to 12, advantageously by carrying out successive exchanges.

The optional exchange with potassium (step d) may be carried out before and/or after exchange with barium (step c). As noted above, it is also possible to agglomerate, in step a), crystalline elements of FAU zeolite already containing barium or potassium or barium and potassium ions (pre-exchange of the cations present in the starting FAU type zeolite, typically sodium cations, with barium or potassium or barium and potassium ions before step a) and omit (or not) steps c) and/or d).

Surprisingly, the applicant observed that the step of cationic exchange, which may be difficult owing to the relative fragility of the structure of the zeolitic crystalline elements, does not affect the intrinsic properties of external surface area and of micropore volume (relative to the weight of the adsorbent once exchanged) of said zeolitic crystalline elements.

After the cationic exchange step or steps, washing is carried out, generally and preferably with water, and then drying of the agglomerate thus obtained.

The activation that follows drying is carried out conventionally, by the methods known by a person skilled in the art, for example at a temperature generally between 100° C. and 400° C., preferably between 200° C. and 300° C. for a time determined as a function of the desired water content and loss on ignition, typically from 1 hour to 6 hours.

The present invention also relates to the uses of the zeolitic adsorbents described above as adsorption agents advantageously able to replace the adsorption agents described in the literature, based on conventional crystals of FAU type zeolite, comprising barium or barium and potassium, the contents of which are respectively expressed in contents of barium oxide or of barium and potassium oxide as noted above, or based on conventional crystals of FAU type zeolite comprising barium or barium and potassium, and notably in the uses listed below:

separation of cuts of C8 aromatic isomers and notably of xylenes,
separation of isomers of substituted toluene such as nitrotoluene, diethyltoluene, toluenediamine, and others,
separation of cresols,
separation of polyhydric alcohols, such as sugars.

The invention notably relates to a method for separating para-xylene from cuts of aromatic isomers with 8 carbon atoms, using, as agent for adsorption of para-xylene, a zeolitic adsorbent comprising barium and/or potassium having a large external surface area characterized by nitrogen adsorption typically greater than 20 $m^2 \cdot g^{-1}$, preferably greater than 40 $m^2 \cdot g^{-1}$, and more preferably between 40 $m^2 \cdot g^{-1}$ and 200 $m^2 \cdot g^{-1}$, and even more preferably between 60 $m^2 \cdot g^{-1}$ and 200 $m^2 \cdot g^{-1}$ inclusive, employed in liquid-phase processes, but also in gas-phase processes.

Thus, it is possible to separate the desired product (para-xylene) by preparative adsorption liquid chromatography (in a batch process), and advantageously continuously in a simulated moving bed, i.e. simulated countercurrent or simulated co-current, and more particularly simulated countercurrent.

The operating conditions of an industrial adsorption unit of the simulated countercurrent type are generally as follows:
number of beds: 6 to 30,
number of zones: at least 4 working zones, each located between a feed point and a withdrawal point,
temperature between 100° C. and 250° C., preferably between 150° C. and 190° C.,
pressure of the industrial unit between the bubble point pressure of the xylenes at the process temperature and 3 MPa,
ratio of the desorbent/feed flow rates between 0.7 and 2.5, for example between 0.9 and 1.8 for a stand-alone adsorption unit and between 0.7 and 1.4 for an adsorption unit combined with a crystallization unit,
recycle ratio between 2.5 and 12, preferably between 3.5 and 6.

On this subject, reference may be made to the teaching of patents U.S. Pat. Nos. 2,985,589, 5,284,992 and 5,629,467.

The operating conditions of an industrial adsorption unit with simulated co-current are in general the same as those operating with simulated countercurrent, apart from the recycle ratio, which is generally between 0.8 and 7. Regarding this aspect, reference may be made to patents U.S. Pat. Nos. 4,402,832 and 4,498,991.

The desorption solvent may be any desorbent known by a person skilled in the art and for which the boiling point is lower than that of the feed, such as toluene, but also a desorbent whose boiling point is higher than that of the feed, such as para-diethylbenzene (PDEB). The selectivity of the adsorbents according to the invention for the adsorption of para-xylene contained in C8 aromatic cuts is optimum when their loss on ignition, measured at 900° C., is preferably less than or equal to 7.7%, preferably between 0 and 7.7%, very preferably between 3.0% and 7.7%, more preferably between 3.5% and 6.5% and even more preferably between 4.5% and 6%, inclusive.

The agglomerated zeolitic adsorbents according to the present invention possess simultaneously the characteristics of the conventional zeolitic adsorbents known from the prior art, notably the mechanical properties and microporosity properties, the characteristics of total mass transfer being maximized relative to zeolitic adsorbents based on conventional crystals.

Moreover, the process for preparing the agglomerated zeolitic adsorbents with FAU zeolite(s) with large external surface area according to the invention is a process that is easy to carry out, rapid and economical and therefore easily industrialized with a minimum of steps.

The following examples illustrate the aims of the invention, and are supplied only indicatively, and are not in any way intended to limit the various embodiments of the present invention.

In the following examples, the physical properties of the agglomerates are evaluated by methods known by a person skilled in the art, of which the main ones are recalled below.

Techniques for Characterization

Granulometry of the Particles:

The number-average diameter of the elements (i.e. crystals) of FAU type zeolite used in step a) and of the elements (i.e. crystals) of zeolite X contained in the agglomerates is estimated by observation with a scanning electron microscope (SEM).

In order to estimate the size of the particles (i.e. crystals) of zeolite in the samples, a set of images is prepared at a magnification of at least 5000. The diameter of at least 200 particles is then measured using dedicated software, for example the Smile View software from the publisher LoGraMi. The precision is of the order of 3%.

Chemical Analysis of the Zeolitic Adsorbents—Si/Al Ratio and Degree of Exchange:

Elemental analysis of the end product obtained at the end of steps a) to f) described above can be carried out by various analytical techniques known by a person skilled in the art. Among these techniques, we may mention the technique of chemical analysis by X-ray fluorescence as described in standard NF EN ISO 12677:2011 on a wavelength-dispersive spectrometer (WDXRF—wavelength-dispersive X-ray fluorescence), for example Tiger S8 from the company Bruker.

X-ray fluorescence is a non-destructive spectral technique exploiting the photoluminescence of the atoms in the X-ray range, to establish the elemental composition of a sample. Excitation of the atoms, generally by a beam of X-rays or by bombardment with electrons, generates specific radiation after the atom returns to the ground state. The X-ray fluorescence spectrum has the advantage of depending very little on the chemical combination of the element, which offers precise determination, both quantitative and qualitative. Conventionally, after calibration for each oxide, a measurement uncertainty of less than 0.4 wt % is obtained.

These elemental chemical analyses make it possible both to verify the Si/Al atomic ratio of the zeolite used in the agglomerate and the Si/Al atomic ratio of the end product obtained at the end of steps a) to f) described above, and to verify the quality of ion exchange described in step c) and in the optional step d). In the description of the present invention, the measurement uncertainty of the Si/Al atomic ratio is ±5%.

The quality of ion exchange is linked to the number of moles of sodium oxide, Na2O, remaining in the zeolitic agglomerate after exchange. More precisely, the degree of exchange with the barium ions is estimated by evaluating the ratio of the number of moles of barium oxide, BaO, to the number of moles of the sum (BaO+$Na_2O$). Similarly, the degree of exchange with the barium and/or potassium ions is estimated by evaluating the ratio of the number of moles of the sum of barium oxide+potassium oxide (BaO+$K_2O$) to the number of moles of the sum (BaO+$K_2O$+$Na_2O$). It should be noted that the contents of the various oxides are given as percentage by weight relative to the total weight of the anhydrous zeolitic adsorbent.

Granulometry of the Zeolitic Adsorbents:

The number-average diameter of the zeolitic adsorbents obtained at the end of step a) of agglomeration and forming is determined by analysing the granulometric distribution of a sample of agglomerate by imaging according to standard ISO 13322-2:2006, using a conveyor belt to allow the sample to pass in front of the camera lens.

The number-average diameter is then calculated from the granulometric distribution by applying standard ISO 9276-2:2001. In the present document, the designation "number-average diameter" or else "size" is employed for the zeolitic agglomerates. The precision is of the order of 0.01 mm for the size range of agglomerates of the invention.

Mechanical Strength of the Zeolitic Adsorbents:

The crushing strength of a bed of zeolitic adsorbents as described in the present invention is characterized by the Shell Method Series SMS1471-74 "Determination of Bulk Crushing Strength of Catalysts. Compression-Sieve Method", combined with the "BCS Tester" apparatus marketed by the company Vinci Technologies. This method, initially intended for the characterization of catalysts from 3 mm to 6 mm, is based on the use of a 425-μm sieve, which will notably make it possible to separate the fines created during crushing. The use of a 425-μm sieve is still suitable for particles with diameter greater than 1.6 mm, but must be adapted according to the granulometry of the agglomerates that we wish to characterize.

The agglomerates of the present invention, generally in the form of beads or extrudates, generally have a number-average diameter or a length, i.e. largest dimension in the case of non-spherical agglomerates, between 0.2 mm and 2 mm, and in particular between 0.2 mm and 0.8 mm and preferably between 0.4 mm and 0.65 mm, inclusive. Consequently, a 100-μm sieve is used in place of the 425-μm sieve mentioned in the Shell standard method SMS1471-74.

The measurement protocol is as follows: a sample of 20 $cm^3$ of agglomerated adsorbents, sieved beforehand with the appropriate sieve (100 μm) and previously dried in the stove for at least 2 hours at 250° C. (instead of 300° C. mentioned in the Shell standard method SMS1471-74), is placed in a metal cylinder of known internal section. An increasing force is imposed in stages on this sample by means of a piston, through a bed of 5 $cm^3$ of steel balls for better distribution of the force exerted by the piston on the agglomerates of adsorbents (using balls with a diameter of 2 mm for particles of a spherical shape with diameter strictly below 1.6 mm). The fines obtained at the different pressure stages are separated by sieving (suitable sieve of 100 μm) and weighed.

The bed crushing strength is determined by the pressure in megapascal (MPa) for which the cumulative amount of fines passing through the sieve increases to 0.5 wt % of the sample. This value is obtained by plotting on a graph the weight of fines obtained as a function of the force applied on the bed of adsorbent and interpolating to 0.5 wt % of cumulative fines. The mechanical crushing strength in the bed is typically between some hundreds of kPa and some tens of MPa and is generally between 0.3 MPa and 3.2 MPa. The precision is conventionally below 0.1 MPa.

Non-Zeolitic Phase of the Zeolitic Adsorbents:

The proportion of non-zeolitic phase NZP, for example residual binder not zeolitized or any other amorphous phase, after zeolitization, is calculated from the following equation:

$$NZP=100-\Sigma(ZP),$$

where ZP represents the sum of the amounts of zeolite X fractions in the sense of the invention.

The amount of zeolite X fractions (degree of crystallinity) is measured by X-ray diffraction analysis, known by a person skilled in the art by the acronym XRD. This analysis is carried out on apparatus made by Bruker, and then the amount of zeolite X fractions is evaluated using the TOPAS software from the company Bruker.

Micropore Volume and External Surface Area:

The crystallinity of the agglomerates is also evaluated by measuring their micropore volume and comparing it with that of a suitable reference (100% crystalline zeolite in conditions of identical cationic treatments or theoretical zeolite). This micropore volume is determined from measurement of the adsorption isotherm of a gas, such as nitrogen, at its liquefaction temperature.

Prior to adsorption, the zeolitic adsorbent is degassed between 300° C. and 450° C. for a time between 9 hours and 16 hours, under vacuum ($P<6.7\times10^{-4}$ Pa). Measurement of the nitrogen adsorption isotherm at 77 K is then carried out on apparatus of the ASAP 2020 M type from Micromeritics, taking at least 35 measurement points at relative pressures with ratio $P/P_0$ between 0.002 and 1.

The micropore volume and the external surface area are determined from the isotherm obtained, by the t-plot method, applying standard ISO 15901-3:2007, and calculating the statistical thickness t with the Harkins-Jura equation. The micropore volume and the external surface area are obtained by linear regression on the points of the t-plot between 0.45 nm and 0.7 nm, from the ordinate at the origin and the linear regression slope, respectively. The micropore volume evaluated is expressed in $cm^3$ of liquid adsorbate per gram of adsorbent. The external surface area is expressed in $m^2$ per gram of adsorbent.

Total Volume of the Macropores and Mesopores:

The total volume of the macropores and mesopores was measured by mercury intrusion porosimetry. The mercury intrusion technique is used for characterizing the intragranular pore volume contained in the pores with diameters above 3.6 nm of the zeolitic granular material, and for measuring its granular density. A mercury porosimeter of type Autopore® 9500 from Micromeritics is used for analysing the distribution of pore volume contained in the macropores with pore diameter larger than 50 nm and in the mesopores between 3.6 nm and 50 nm. The volume fraction of the macropores is calculated by dividing the pore volume contained in the macropores by the total volume of the macropores and mesopores.

The experimental method, described in the operating manual of the apparatus, consists of putting a sample of adsorbent (of known loss on ignition), weighed beforehand, in a cell of the porosimeter, then, after prior degassing (evacuation pressure of 30 µm Hg for at least 10 min), filling the cell with mercury at a given pressure (0.0036 MPa), and then applying a pressure increasing in stages up to 400 MPa to cause gradual penetration of the mercury into the pore network of the sample.

The relation between the pressure applied and the diameter of the pores is established by assuming cylindrical pores, a contact angle between the mercury and the wall of the pores of 140° and a surface tension of mercury of 485 dynes/cm.

Loss on Ignition of the Zeolitic Adsorbents:

The loss on ignition is determined in oxidizing atmosphere, by calcination of the sample in air at a temperature of 900° C.±25° C., following the procedure described in standard NF EN 196-2 (April 2006). The standard deviation of measurement is less than 0.1%.

Characterization of the Liquid-Phase Adsorption by Breakthrough:

The technique used for characterizing the liquid-phase adsorption of molecules on a porous solid is the so-called breakthrough technique, described by Ruthven in "*Principles of Adsorption and Adsorption Processes*" (John Wiley & Sons, (1984), Chapters 8 and 9), which defines the technique of "breakthrough curves" as investigation of the response to injection of an increment of adsorbable constituents.

Analysis of the mean exit time (first moment) of the breakthrough curves supplies information on the quantities adsorbed and also makes it possible to evaluate the selectivities, i.e. the separation factor, between two adsorbable constituents. Injection of a non-adsorbable constituent used as tracer is recommended for estimating the non-selective volumes. Analysis of the dispersion (second moment) of the breakthrough curves makes it possible to evaluate the height equivalent to a theoretical plate, based on the representation of a column by a finite number of ideally stirred hypothetical reactors (theoretical stages), which is a direct measure of the axial dispersion and resistance to mass transfer of the system.

Example 1: Synthesis of FAU Zeolite with High External Surface Area

The FAU zeolite with high external surface area is synthesized directly as described in the article Inayat et al., *Angew. Chem. Int. Ed.*, (2012), 51, 1962-1965).

Step 1): Preparation of the Growth Gel in a Reactor Stirred with an Archimedes Screw at 300 rev·min$^{-1}$.

In a stainless-steel reactor equipped with a heating jacket, a temperature probe and a stirrer, a growth gel is prepared by mixing an aluminate solution containing 119 g of sodium hydroxide (NaOH) with 128 g of alumina trihydrate ($Al_2O_3$, 3$H_2O$, containing 65.2 wt % of $Al_2O_3$) and 195.5 g water at 25° C. in 25 minutes with a stirring speed of 300 rev·min$^{-1}$ in a silicate solution containing 565.3 g of sodium silicate, 55.3 g of NaOH and 1997.5 g of water at 25° C.

The stoichiometry of the growth gel is as follows: 3.48 $Na_2O/Al_2O_3/3.07$ $SiO_2/180$ $H_2O$. The growth gel is homogenized by stirring at 300 rev·min$^{-1}$, for 25 minutes at 25° C.

Step 2): Adding the Structure-Forming Agent to the Reaction Mixture 27.3 g of solution of TPOAC at 60% in MeOH is introduced into the reaction mixture, at a stirring speed of 300 rev·min$^{-1}$ (molar ratio TPOAC/$Al_2O_3$=0.04). After homogenization for 5 minutes, the stirring speed is lowered to 50 rev·min$^{-1}$.

Step 3): Ripening Phase

The reaction mixture is stirred at 50 rev·min$^{-1}$ at 25° C. for 22 hours, then crystallization is started.

Step 4): Crystallization

The stirring speed is maintained at 50 rev·min$^{-1}$, and the setting for the reactor jacket is fixed at 80° C. so that the temperature of the reaction mixture rises to 75° C. in 80 minutes. After maintaining a plateau of 75° C. for 72 hours, the reaction mixture is cooled by circulating cold water in the jacket to stop crystallization.

Step 5): Filtration/Washing

The solids are recovered on a frit and then washed with deionized water to neutral pH.

Step 6): Drying/Calcination

For characterization of the product, it is dried in a stove at 90° C. for 8 hours; the loss on ignition of the dried product is 22 wt %.

Calcination of the dried product, required for releasing both the microporosity (water) and the mesoporosity by expelling the structure-forming agent, is carried out with the following temperature profile: temperature increase to 200° C. in 30 minutes, then 1-hour plateau at 200° C., then 3 hours of temperature rise to 550° C., and finally plateau at 550° C. for 1.5 hours.

The micropore volume and the external surface area, measured by the t-plot method from the nitrogen adsorption isotherm at 77 K after degassing under vacuum at 400° C. for 10 hours, are 0.260 cm$^3$·g$^{-1}$ and 90 m$^2$·g$^{-1}$ respectively. The number-average diameter of the crystalline elements is 4.5 µm.

Hereinafter, a weight expressed in anhydrous equivalent signifies a weight of product minus its loss on ignition.

Example 2: (Comparative)

A homogeneous mixture is prepared consisting of 1600 g anhydrous equivalent of crystals of zeolite X with number-average diameter of 1.0 µm, 350 g anhydrous equivalent of kaolin, 130 g of colloidal silica sold under the trade name Klebosol® 30 (containing 30 wt % of $SiO_2$ and 0.5% of $Na_2O$), as well as the amount of water necessary for extrusion of the mixture. The loss on ignition of the paste before extrusion is 44%.

Extrudates are formed with a diameter of 1.6 mm. The extrudates are dried overnight in a ventilated stove at 80° C. They are then calcined for 2 hours at 550° C. under a nitrogen stream, then for 2 hours at 550° C. under a stream of decarbonated dry air, and then crushed to recover grains with an equivalent diameter of 0.4 mm.

These granules are exchanged by means of a 0.5 M solution of barium chloride at 95° C. in 4 steps. At each step, the ratio of the volume of solution to the weight of solid is 20 mL·g$^{-1}$ and exchange is continued for 4 hours each time.

Between each exchange, the solid is washed several times to remove excess salt. It is then activated at a temperature of 250° C. for 2 hours under a nitrogen stream.

The degree of barium exchange is 97% and the loss on ignition (measured at 900° C.) is 5.4%. The micropore volume and the external surface area, measured by the t-plot method from the nitrogen adsorption isotherm at 77 K after degassing under vacuum at 400° C. for 10 hours, are 0.226 $cm^3 \cdot g^{-1}$ and 16.7 $m^2 \cdot g^{-1}$ respectively.

The total volume of the macropores and mesopores measured by mercury porosimetry is 0.32 $cm^3 \cdot g^{-1}$. The volume fraction of the macropores to the total volume of the macropores and mesopores is equal to 0.87.

A breakthrough test (frontal chromatography) is then performed on these adsorbents to evaluate their efficacy. The amount of adsorbent used for this test is about 34 g.

The procedure for obtaining the breakthrough curves is as follows:
Filling the column with the sieve and placing it in the test bench.
Filling with the solvent at room temperature.
Gradual increase to the adsorption temperature under solvent flow (5 $cm^3$/min).
Injection of solvent at 30 $cm^3$/min when the adsorption temperature is reached.
Solvent/feed exchange for injecting the feed (30 $cm^3 \cdot min^{-1}$).
Injection of the feed is then maintained for a sufficient time to attain thermodynamic equilibrium (i.e. until the concentration of solvent in the effluent is zero).
Collection and analysis of the breakthrough effluent.

The solvent used is para-diethylbenzene. The composition of the feed is as follows:
para-xylene: 45 wt %
meta-xylene: 45 wt %
iso-octane: 10 wt % (the latter is used as tracer for estimating the non-selective volumes and is not involved in the separation)

A first test is carried out with an adsorption temperature of 175° C. and a second test is carried out with an adsorption temperature of 160° C. The pressure is sufficient for the feed to remain in the liquid phase, i.e. 1 MPa.

The selectivity for para-xylene relative to meta-xylene is calculated from the mass balance. The breakthrough results are reported in Table 1 below:

TABLE 1

| T (° C.) | selectivity PX/MX | Adsorption capacity ($cm^3 \cdot g^{-1}$) | Empty drum velocity ($cm \cdot s^{-1}$) | HEPT PX (cm) |
|---|---|---|---|---|
| 175 | 3.35 | 0.191 | 1.32 | 6.31 |
| 160 | 3.72 | 0.189 | 1.29 | 19.23 |

Legend
LOI = loss on ignition
T (° C.) = adsorption temperature
Adsorption capacity expressed as $cm^3$ of $C_8$-aromatics adsorbed per gram of adsorbent
Empty drum velocity = interstitial velocity (flow rate/column section)
HEPT = Height Equivalent to a Theoretical Plate (in cm)
PX = para-xylene;
MX = meta-xylene The mechanical strength is also measured by the method presented in the description of the invention. The pressure required to obtain 0.5% of fines is 2.2 MPa.

Example 2 Bis: (Comparative)

In this example, an adsorbent according to the prior art (FR2789914) is prepared and tested. Example 2 of FR2789914 was reproduced identically using industrial crystals of zeolite NaX (powder with the trade name G5, with atomic ratios Si/Al=1.25 and Na/Al=1, and with number-average diameter of 2.1 µm and colloidal silica sold under the trade name Klebosol® 30 (previously marketed under the name Cecasol® 30).

The adsorbent thus prepared according to example 2 of FR2789914 has a degree of barium exchange of 97.4% and a loss on ignition (measured at 900° C.) of 5.2%. The micropore volume and the external surface area are measured from the nitrogen adsorption isotherm at 77 K after degassing under vacuum at 400° C. for 10 hours. The micropore volume measured by the Dubinin-Radushkevitch method and that measured by the t-plot method are identical and equal to 0.248 $cm^3 \cdot g^{-1}$ and the external surface area, measured by the t-plot method, is 2 $m^2 \cdot g^{-1}$.

The total volume of the macropores and mesopores measured by mercury porosimetry is 0.304 $cm^3 \cdot g^{-1}$. The volume fraction of the macropores to the total volume of the macropores and mesopores is equal to 0.94.

A breakthrough test (frontal chromatography) is then performed on these adsorbents to evaluate their efficacy. The amount of adsorbent used for this test is about 35 g. The test is carried out only at an adsorption temperature of 175° C.

The composition of the feed and the procedure for obtaining the breakthrough curves are identical to that described in example 2. The selectivity for para-xylene relative to meta-xylene is calculated from the mass balance. The breakthrough results are reported in Table 2 below:

TABLE 2

| T (° C.) | selectivity PX/MX | Adsorption capacity ($cm^3 \cdot g^{-1}$) | Empty drum velocity ($cm \cdot s^{-1}$) | HEPT PX (cm) |
|---|---|---|---|---|
| 175 | 3.60 | 0.205 | 1.3 | 38.1 |

Legend
T (° C.) = adsorption temperature
Adsorption capacity expressed in $cm^3$ of $C_8$-aromatics adsorbed per gram of adsorbent
Empty drum velocity = interstitial velocity (flow rate/column section)
HEPT = Height Equivalent to a Theoretical Plate (in cm)
PX = para-xylene;
MX = meta-xylene Example 2 Ter: (Comparative)

In this example, an adsorbent according to the prior art is prepared and tested. Comparative example 3 of FR2903978 according to the prior art FR2789914 is reproduced identically using industrial zeolite NaX crystals having an atomic ratio Si/Al equal to 1.25, an atomic ratio Na/Al equal to 1, and a measured number-average diameter of the crystals equal to 2.1 µm, and colloidal silica sold under the trade name Klebosol® 30 (previously under the name Cecasol® 30).

The adsorbent thus prepared has a degree of barium exchange of 95% and a loss on ignition (measured at 900° C.) of 6.0%. The micropore volume and the external surface area are measured from the nitrogen adsorption isotherm at 77 K after degassing under vacuum at 400° C. for 10 hours. The micropore volume measured by the Dubinin-Radushkevitch method and that measured by the t-plot method are identical and equal to 0.252 $cm^3 \cdot g^{-1}$ and the external surface area, measured by the t-plot method, is 3 $m^2 \cdot g^{-1}$.

The total volume of the macropores and mesopores measured by mercury porosimetry is 0.280 $cm^3 \cdot g^{-1}$. The volume fraction of the macropores to the total volume of the macropores and mesopores is equal to 0.93.

A breakthrough test (frontal chromatography) is then performed on these adsorbents to evaluate their efficacy. The amount of adsorbent used for this test is about 35 g.

The composition of the feed and the procedure for obtaining the breakthrough curves are identical to that described in example 2. The test is carried out only at an adsorption temperature of 175° C.

The selectivity for para-xylene relative to meta-xylene is calculated from the mass balance. The breakthrough results are reported in Table 3 below:

TABLE 3

| T (° C.) | selectivity PX/MX | Adsorption capacity (cm$^3 \cdot$ g$^{-1}$) | Empty drum velocity (cm $\cdot$ s$^{-1}$) | HEPT PX (cm) |
|---|---|---|---|---|
| 175 | 3.41 | 0.199 | 1.3 | 17.6 |

Legend
T (° C.) = adsorption temperature
Adsorption capacity expressed in cm$^3$ of C$_8$-aromatics adsorbed per gram of adsorbent
Empty drum velocity = interstitial velocity (flow rate/column section)
HEPT = Height Equivalent to a Theoretical Plate (in cm)
PX = para-xylene;
MX = meta-xylene The mechanical strength is also measured by the method presented in the description of the invention. The pressure required for obtaining 0.5% of fines is 2.6 MPa.

Example 3: (According to the Invention)

In the same way as in example 2, a homogeneous mixture is prepared consisting of 1600 g anhydrous equivalent of crystals of zeolite X synthesized according to the procedure in example 1, 350 g anhydrous equivalent of kaolin, 130 g of colloidal silica sold under the trade name Klebosol® 30 (containing 30 wt % of SiO$_2$ and 0.5% of Na$_2$O) plus the amount of water to allow extrusion of the mixture. The loss on ignition of the paste before extrusion is 44%.

Extrudates with a diameter of 1.6 mm are formed. The extrudates are dried overnight in a ventilated stove at 80° C. They are then calcined for 2 hours at 550° C. under a nitrogen stream, then for 2 hours at 550° C. under a stream of decarbonated dry air and then are crushed, recovering grains with an equivalent diameter of 0.4 mm.

Barium exchange is performed in operating conditions identical to those in example 2, except for the concentration of the BaCl$_2$ solution, which is 0.7 M, followed by washing and then drying at 80° C. for 2 hours and finally activation at 250° C. for 2 hours under a nitrogen stream.

The degree of barium exchange is 97% and the loss on ignition (measured at 900° C.) is 5.5%. The micropore volume and the external surface area, measured by the t-plot method from the nitrogen adsorption isotherm at 77 K after degassing under vacuum at 400° C. for 10 hours, are 0.192 cm$^3 \cdot$g$^{-1}$ and 70 m$^2 \cdot$g$^{-1}$ respectively.

The total volume of the macropores and mesopores measured by mercury porosimetry is 0.33 cm$^3 \cdot$g$^{-1}$. The volume fraction of the macropores to the total volume of the macropores and mesopores is equal to 0.6.

A breakthrough test (frontal chromatography) is then performed on these adsorbents to evaluate their efficacy. The amount of adsorbent used for this test is about 34 g.

The procedure as well as the composition of the feed are identical to those in example 2. The selectivity for para-xylene relative to meta-xylene is calculated from the mass balance. The breakthrough results are presented in Table 4 below:

TABLE 4

| T (° C.) | selectivity PX/MX | Adsorption capacity (cm$^3 \cdot$ g$^{-1}$) | Empty drum velocity (cm/s) | HEPT PX (cm) |
|---|---|---|---|---|
| 175 | 2.66 | 0.180 | 1.32 | 2.64 |
| 160 | 2.78 | 0.179 | 1.29 | 3.35 |

Legend
T (° C.) = adsorption temperature
Adsorption capacity expressed in cm$^3$ of C$_8$-aromatics adsorbed per gram of adsorbent
Empty drum velocity = interstitial velocity (flow rate/column section)
HEPT = Height Equivalent to a Theoretical Plate (in cm)
PX = para-xylene;
MX = meta-xylene The mechanical strength is also measured by the method presented in the description of the invention. The pressure required for obtaining 0.5% of fines is 2.1 MPa.

Relative to the results obtained with the adsorbent in examples 2, 2bis and 2ter, it can be seen that there is a definite improvement in mass transfer, as the height equivalent to a theoretical plate has decreased considerably.

What is claimed is:

1. A method for separating para-xylene from cuts of aromatic isomers with 8 carbon atoms, using, as an agent for adsorption of para-xylene, a zeolitic adsorbent comprising at least one FAU zeolite and comprising at least one of barium and potassium, wherein the external surface area of said zeolitic adsorbent, measured by nitrogen adsorption, is greater than 20 m$^2 \cdot$g$^{-1}$, said method comprising:
   contacting aromatic isomers with 8 carbon atoms with said zeolitic adsorbent; and
   adsorbing para-xylene.

2. A method according to claim 1, wherein the method is in the liquid phase, and wherein adsorbing para-xylene is performed in the presence of a desorbent.

3. A method according to claim 2, wherein the desorbent is selected from the group consisting of toluene and para-diethylbenzene.

4. A method according to claim 1, wherein the method is a simulated moving-bed method.

5. A method according to claim 1, wherein the method is a simulated countercurrent moving-bed method.

6. A method according to claim 1, wherein the zeolitic adsorbent has a content of barium oxide (BaO) above 10% relative to the total weight of the zeolitic adsorbent and a barium content between 23% and 42%, inclusive, by weight relative to the total weight of the zeolitic adsorbent.

7. A method according to claim 1, wherein the zeolitic adsorbent has a content of potassium oxide K$_2$O below 25% by weight relative to the total weight of the zeolitic adsorbent.

8. A method according to claim 1, wherein said FAU zeolite has an Si/Al atomic ratio between 1.00 and 1.50 inclusive.

9. A method according to claim 1, wherein no zeolitic structure other than a faujasite structure is detected in the zeolitic adsorbent by X-ray diffraction.

10. A method according to claim 1, wherein the fraction by weight of FAU zeolite is greater than or equal to 80% relative to the total weight of zeolitic adsorbent.

11. A method according to claim 1, wherein the zeolitic adsorbent has a loss on ignition measured at 900° C. according to standard NF EN 196-2 of less than or equal to 7.7%.

12. A method according to claim 1, wherein the zeolitic adsorbent has a total volume of macropores and mesopores, measured by mercury intrusion porosimetry, of between 0.15 cm$^3 \cdot$g$^{-1}$ and 0.5 cm$^3 \cdot$g$^{-1}$.

13. A method according to claim 1, wherein the zeolitic adsorbent has a volume fraction of macropores of between 0.2 and 1 of the total volume of macropores and mesopores, inclusive.

14. A method according to claim 1, wherein the zeolitic adsorbent has a number-average diameter of crystalline elements of between 0.1 μm and 20 μm, inclusive.

15. A method for separating polyhydric alcohols, using an adsorbent, wherein the adsorbent is a zeolitic adsorbent, said method comprising:

contacting polyhydric alcohols with a zeolitic adsorbent as defined in claim 1.

16. The method of claim 15, wherein the polyhydric alcohols are sugars.

17. A method for separating isomers of substituted toluene, using an adsorbent, wherein the adsorbent is a zeolitic adsorbent, said method comprising:

contacting isomers of substituted toluene with a zeolitic adsorbent as defined in claim 1.

18. The method of claim 17, wherein the isomers of substituted toluene are selected from the group consisting of isomers of nitrotoluene, diethyltoluene, and toluenediamine.

19. A method for separating cresols using an adsorbent, wherein the adsorbent is a zeolitic adsorbent, said method comprising:

contacting cresols with a zeolitic adsorbent as defined in claim 1.

* * * * *